United States Patent
Brinkmann-Rengel et al.

(10) Patent No.: US 6,639,033 B1
(45) Date of Patent: Oct. 28, 2003

(54) N-OXYL RADICALS

(75) Inventors: Susanne Brinkmann-Rengel, Ober-Olm (DE); Sylke Haremza, Neckargemünd (DE); Heinz Friedrich Sutoris, Frankenthal (DE); David Christie, Mannheim (DE); Roman Benedikt Raether, Limburgerhof (DE); Jizhuang Cao, Shanghai (CN)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/048,988

(22) PCT Filed: Aug. 17, 2000

(86) PCT No.: PCT/EP00/08040

§ 371 (c)(1), (2), (4) Date: Feb. 19, 2002

(87) PCT Pub. No.: WO01/12614

PCT Pub. Date: Feb. 22, 2001

(30) Foreign Application Priority Data

Aug. 18, 1999 (DE) .......................................... 199 39 031

(51) Int. Cl.$^7$ .............................. C08F 2/00; C08F 12/04
(52) U.S. Cl. ...................... 526/205; 526/204; 526/217; 526/220; 526/346; 526/347.1; 525/256; 525/267
(58) Field of Search ................................. 526/204, 205, 526/217, 220, 346, 347.1; 525/256, 267

(56) References Cited

U.S. PATENT DOCUMENTS

| | | |
|---|---|---|
| 3,943,098 A | 3/1976 | Rody |
| 4,061,631 A | 12/1977 | Rody |
| 4,528,370 A | 7/1985 | Lai |
| 4,581,429 A | 4/1986 | Solomon et al. |
| 5,021,481 A | 6/1991 | Galbo et al. |
| 5,322,912 A | 6/1994 | Georges et al. |
| 5,322,960 A | 6/1994 | Sakamoto et al. |
| 5,412,047 A | 5/1995 | Georges et al. |
| 5,891,660 A | 4/1999 | Shiga et al. |
| 6,281,311 B1 | 8/2001 | Lai et al. |

FOREIGN PATENT DOCUMENTS

| | | |
|---|---|---|
| DE | 23 51 865 | 4/1974 |
| DE | 197 35 225 | 2/1999 |
| EP | 0 135 280 | 3/1985 |
| EP | 0 742 437 | 11/1996 |
| EP | 0 869 137 | 10/1998 |

OTHER PUBLICATIONS

T. Yoshioka et al., Bulletin of the Chemical Society of Japan, vol. 45, No. 6, pp. 1855–1860, 1972.
S.D. Rychnovsky et al., Journal of Organic Chemistry, vol. 63, No. 18, pp. 6363–6374, 1998.
V.A. Livshits et al., Colloids and Surfaces A: Physicochemical and Engineering Aspects, vol. 72, pp. 313–320, 1993.
J.T. Lai, Synthesis, No. 2, pp. 122–123, 1984.

*Primary Examiner*—Fred Teskin
(74) *Attorney, Agent, or Firm*—Oblon, Spivak, McClelland, Maier & Neustadt, P.C.

(57) ABSTRACT

The present invention provides a process for the free radical polymerization of one or more ethylenically unsaturated monomers, said process comprising polymerizing one or more ethylenically unsaturated monomers in the presence of one or more N-oxyl radicals of formula II,

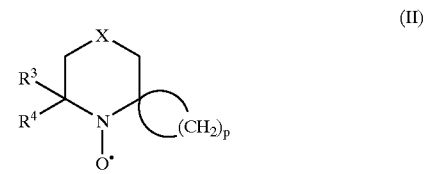

(II)

wherein
X is S, $NR^5$, O, SO or $SO_2$,
$R^5$ is $C_1$–$C_{20}$-alkyl or $C_5$–$C_8$-cycloalkyl and
$R^3$ and $R^4$ independently of one another, are $C_1$–$C_4$-alkyl, phenyl, naphthyl or an aromatic five-membered ring, or $R^3$ and $R^4$ together are —$(CH_2)_o$— and p and o, independently of one another, are an integer from 2 to 7.

14 Claims, No Drawings

N-OXYL RADICALS

The present invention relates to N-oxyl radicals, N-oxyl radical formers and their use in the free radical polymerization of ethylenically unsaturated monomers.

N-oxyl radicals and N-oxyl radical formers which are derived from a secondary amine which carries no hydrogen atoms on the α-carbon atom are known. They are or form extremely stable free radicals and as a rule can be prepared as a pure substance.

Such stable N-oxyl radicals are used, inter alia, as inhibitors of undesired free radical polymerization (cf. for example U.S. Pat. No. 5,322,960). A further use of such stable N-oxyl radicals consists in the fact that their presence permits a certain control of free radical polymerizations of compounds (monomers) having at least one ethylenically unsaturated group (cf. for example EP-A 135280, U.S. Pat. No. 5,412,047 and U.S. Pat. No. 5,322,912).

In fact, free radical polymerizations of monomers usually have the disadvantage that the molecular weight of the polymer chains does not increase linearly with the conversion in the polymerization and that the polymer chains of the resulting polymer do not as a rule have a uniform molecular weight, i.e. the polymer obtainable by free radical polymerization is as a rule not monodispersed with respect to the property of molecular weight but usually has a polydispersity index PDI in this context of $\geq 2$ (PDI=$\overline{M_w}/\overline{M_n}$, where $\overline{M_w}$ is the weight-average molecular weight of the polymer and $\overline{M_n}$=is the number average molecular weight of the polymer). Both of the abovementioned phenomena adhere to determination reactions as a result of the irreversible combination of growing free radical polymer chain ends.

The controlled influence of stable N-oxyl radicals (which are usually not capable of initiating a free radical polymerization of monomers) is presumably due to the fact that the stable N-oxyl radicals do not irreversibly terminate but only temporarily block reactive free radical ends of a growing polymer-chain. This results in a reduction in the steady-state concentration of growing free radical polymer chain ends, which reduces the possibility of an irreversible termination of the chain growth of two growing polymer chain ends. This leads on average to polymer chains growing (ideally linearly) with the conversion in the polymerization. The latter results in an average molecular weight of the resulting polymer which increases (ideally linearly) for the conversion of the polymerization and has a polydispersity index frequently <2. A controlled free radical polymerization carried out as described thus permits the preparation of tailor-made polymers having a specific molecular weight and appropriately tailored physical properties. Furthermore, it opens up the possibility of the preparation of block copolymers.

The stable N-oxyl radicals may be added to the polymerization system as such and/or in the form of N-oxyl radical formers. In the first case, the addition of classical free radical polymerization initiators or initiation by heat or high-energy radiation is usually essential for initiating the controlled free radical polymerization. In the second case, the polymerization can be initiated simply by the free radicals formed in addition to the stable N-oxyl radicals in thermal decomposition of the N-oxyl radical formers.

Stable free N-oxyl radicals used todate are, inter alia, TEMPO [(1): 2,2,6,6-tetramethylpiperidin-1-oxyl] and 4-OH-TEMPO [(2): 4-hydroxy-2,2,6,6-tetramethylpiperidin-1-oxyl].

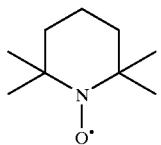

(1)

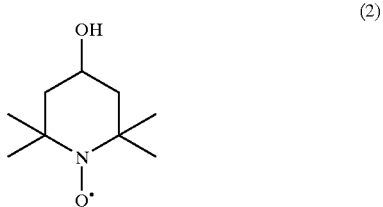

(2)

However, the disadvantage of the abovementioned N-oxyl radical is that their range of-use is limited essentially to the polymerization of systems which contain styrene monomers or a mixture of styrene monomers and other monomers. Nonstyrene monomers cannot be expediently subjected to homopolymerization in the presence of TEMPO or 4-OH-TEMPO.

U.S. Pat. No. 4,528,370 relates to polysubstituted 2-morpholones. When the term nitroxyl compounds is used in this publication, only the preparation of the nitroxyls of precursor compounds in the form of substituted hydroxyethylaminoacetates is mentioned.

EP-A-0 869 137 discloses a polymerization process for the preparation of (meth)acrylate-containing homopolymers or block copolymers in the presence of specific nitroxyls of the piperazinone or morpholone structure type.

However, the known free radical polymerization processes in the presence of nitroxyl radicals have the disadvantage that long reaction times are required for achieving practicable conversions.

DE-A-2 351 865 discloses, inter alia, the compound 2,2,6,6-tetramethyl-1-aza-4-thiacyclohexane-1,4,4-trioxide. The use of this compound for controlling free radical polymerizations is neither taught nor suggested.

It is an object of the present invention to provide novel N-oxyl radicals or formers of novel N-oxyl radicals, in the presence of which the controlled free radical polymerization leads to relatively high conversions in relatively short times. They should furthermore be suitable for carrying out controlled free radical polymerizations of nonstyrene monomers, in particular of esters of acrylic and/or methacrylic acids.

We have found that this object is achieved, according to the invention, by N-oxyl radicals of the formula I

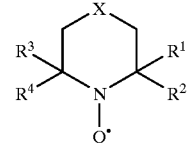

(I)

where X is S, NR$^5$, O or SO and
R$^1$, R$^2$, R$^3$, R$^4$ and R$^5$ independently of one another, are organic radicals or
R$^1$ and R$^2$ and/or R$^3$ and R$^4$ together with the carbon atom carrying them, are a ring consisting at least of 3 atoms.

We have found that the object is furthermore achieved by a process for the free radical polymerization of ethylenically unsaturated monomers, wherein the polymerization is carried out in the presence of N-oxyl radicals of the formula I, where X may additionally be $SO_2$.

In a preferred embodiment, the N-oxyl radicals of the formula I comprise a spiro ring system formed from $R^1$ and $R^2$ and/or $R^3$ and $R^4$, together with the carbon atom carrying them, particularly preferably from $R^1$ and $R^2$, together with the carbon atom carrying them. Two nonneighboring ring atoms in the ring may be bridged via a divalent organic radical and/or the ring may be fused to a further ring. Expediently, the ring formed from $R^1$ and $R^2$ or $R^3$ and $R^4$, together with the carbon atom carrying them, consists of from 3 to 10, preferably of three, five, six or seven, atoms, the free valences of the atoms forming the ring being saturated with hydrogen and/or organic radicals, preferably $C_1$–$C_{20}$-alkyl, especially $C_1$–$C_4$-alkyl (e.g. methyl, ethyl, n-propyl, isopropyl, n-butyl, isobutyl and tert-butyl). However, aryl groups are also suitable as such saturating radicals. Among these, the phenyl and the naphthyl group are preferred. Usually, the ring is a saturated ring and generally the ring-forming atoms are carbon atoms, but the ring-forming atoms may also include, for example, one or two heteroatoms, such suitable heteroatoms being in particular, N, O and/or S.

The present invention relates in particular to N-oxyl radicals of the formula I, where $R^1$, $R^2$, $R^3$, $R^4$ and $R^5$ independently of one another, are $C_1$–$C_{20}$-alkyl, $C_5$–$C_8$-cycloalkyl, $C_7$–$C_{20}$-aralkyl, unsubstituted or substituted $C_6$–$C_{10}$-aryl, heteroaryl, $$—R^6—OR^7, \quad —R^6—O—[CH_2—CH—O]_n—R^7,$$
$$\quad\quad\quad\quad\quad\quad\quad\quad\quad\quad\quad\quad |$$
$$\quad\quad\quad\quad\quad\quad\quad\quad\quad\quad (CH_2)_k$$
$$\quad\quad\quad\quad\quad\quad\quad\quad\quad\quad |$$
$$\quad\quad\quad\quad\quad\quad\quad\quad\quad\quad H$$

$$—R^6—O—\overset{O}{\underset{\|}{C}}—R^8 \quad —R^6—OSiR^8{}_3, \quad —R^9—\overset{O}{\underset{\|}{C}}—OR^{10},$$

$$—R^9—\overset{O}{\underset{\|}{C}}—NR^7{}_2 \quad oder—R^9—CN$$

where
  $R^6$ is straight-chain or branched $C_1$–$C_{20}$-alkylene,
  $R^7$ in each case independently H, $C_1$–$C_{20}$-alkyl, $C_3$–$C_{20}$-cycloalkyl which may be interrupted by oxygen atoms, or aryl,
  $R^8$ in each case independently $C_1$–$C_{20}$-alkyl or aryl,
  $R^9$ is a chemical bond or straight-chain or branched $C_1$–$C_{20}$-alkylene, and
  $R^{10}$ is H, $C_1$–$C_{20}$-alkyl, aryl or an alkali metal,
  k is 0 or 1 and
  n is an integer from 1 to 100,
  or $R^3$ and $R^4$ together are an oxygen atom and/or $R^1$ and $R^2$ and/or $R^3$ and $R^4$, together where the carbon atom carrying them, form a carbocyclic ring which comprises 3 to 10 atoms and in which 1 or 2 carbon atoms may be replaced by O, S or N and/or in which two nonneighboring atoms may be bridged via a divalent organic radical, preferably $C_1$–$C_3$-alkylene, and/or which may be fused to a further, preferably 5- or 6-membered ring.

If aryl radicals are substituted, suitable substituents include $C_1$- to $C_6$-alkyl, $C_1$- to $C_6$-alkoxy, —$SO_3H$, $SO_3M$ (where M is an alkali metal, e.g. Na or K) or $NO_2$.

Heteroaryl is preferably a heteroaromatic five-membered ring having 1, 2, 3 or 4 heteroatoms selected from O, S or N.

$R^1$ and $R^2$ and/or $R^3$ and $R^4$, together with the carbon atom carrying them, may form, for example, the following ring systems:

Particularly preferred N-oxyl radicals are of the formula II:

(II)

where X has the abovementioned meanings,
  $R^3$ and $R^4$, independently of one another, are $C_1$–$C_4$-alkyl, phenyl, naphthyl or an aromatic five-membered ring or $R^3$ and $R^4$ together are -$(CH_2)_o$— and p and o, independently of one another, are an integer from 2 to 8, preferably from 4 to 6.

The preparation of compounds I is possible by various synthesis steps known per se. As a rule, it is carried out via a secondary amine whose $$\diagdown\!\!\!\!\diagup \text{N—H}$$

group is converted by oxidation into the corresponding $$\diagdown\!\!\!\!\diagup \text{N—O}^\bullet$$

N-oxyl group.

Suitable oxidizing agents are peroxides, such as $H_2O_2$, tert-butyl hydroxyperoxide, cumyl hydroperoxide, peracids, such as metachloroperbenzoic acid, α-chloroperbenzoic acid, peracetic acid, p-nitrobenzoic acid, perbenzoic acid or magnesium monoperoxyphthalate. The oxidation can be carried out in an inert solvent, such as $CH_2Cl_2$, petroleum ether, toluene, xylene or benzene.

The starting amines of the formula IV (IV)

where $R^1$, $R^2$, $R^3$, $R^4$ and $R^5$ have the abovementioned meanings, can be obtained, for example as follows (where X=O):

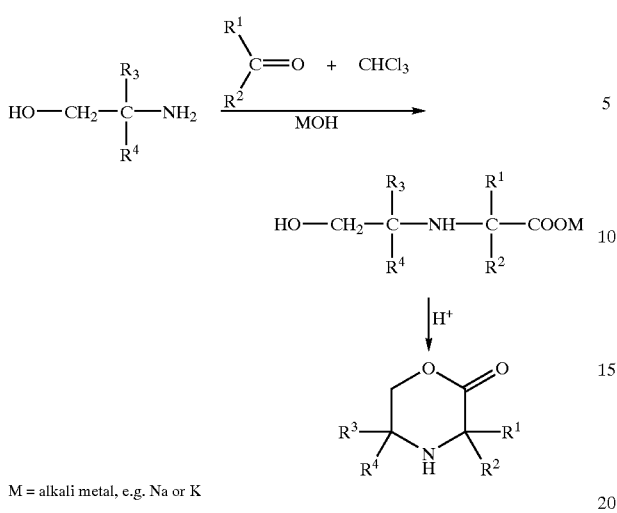

M = alkali metal, e.g. Na or K

Here, a mono- or disubstituted 2-aminoethanol is reacted with a cyclic ketone and a haloform, e.g. chloroform or bromoform, in the presence of an alkali metal hydroxide, if required under phase transfer conditions, to give a substituted alkali metal hydroxyethylaminoacetate. This can be cyclized under acid catalysis. Regarding the reaction conditions, reference may be made to U.S. Pat. No. 4,528,370.

The amine formed can be reduced, for example, with lithium aluminum hydride and converted into a diol.

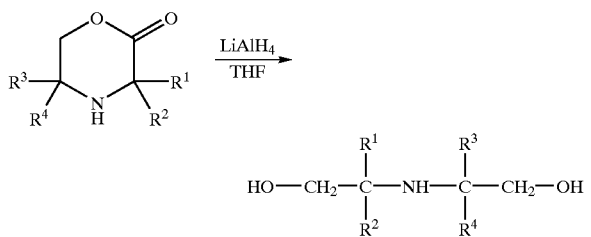

The cyclization under acid catalysis, for example with methanesulfonic acid, is then carried out.

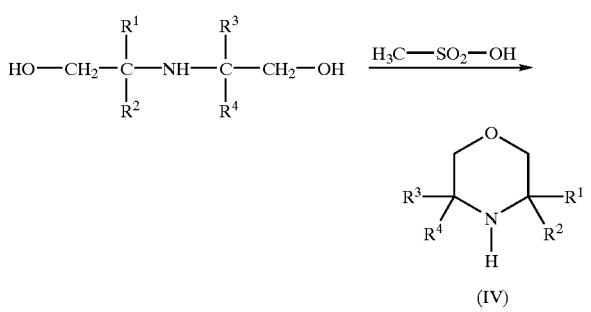

Regarding the reaction conditions, reference may be made to J. T. Lai, Synthesis 2 (1984), 122–124. Amines of the formula IV, where X is S, $NR^5$, SO or $SO_2$, can be prepared in an analogous manner from the corresponding starting materials.

Instead of converting the amine directly into a novel N-oxyl radical, it can also be subjected, in a manner known per se, to various modifications in order thereafter to obtain N-oxyl radicals modified oxidatively in a corresponding manner (however, it is of course also possible to modify the N-oxyl radical as such).

The present invention furthermore relates to N-oxyl radical formers, which form a novel N-oxyl radical as a fragment by homolytic cleavage, for example by thermolysis, of a chemical bond. They are of the formula III

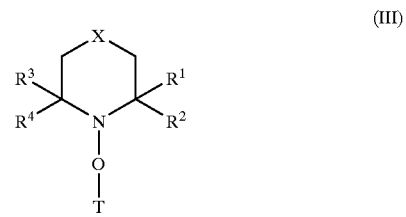

where X, $R^1$, $R^2$, $R^3$ and $R^4$ have the abovementioned meanings and T is an organic radical having a molecular weight of 15 or more, preferably from 29 to 500.000. T is, is for example,

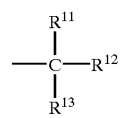

where $R^{11}$, $R^{12}$ and $R^{13}$, independently of one another, are hydrogen, $C_1$–$C_4$-alkyl, phenyl, or a cyano or ester group, or polymeric chain comprising units of ethylenically unsaturated monomers. The radical $C(R^{11})(R^{12})(R^{13})$ is, for example, methyl, ethyl, tert-butyl, cyclohexyl, octyl, phenyl, $C(CN)(CH_3)_2$, $CHPhCH_3$ or $CH(CH_3)COOR$, (where R is, for example, $C_1$–$C_4$-alkyl).

The N-oxyl radical formers III are obtainable by reacting N-oxyl radicals of the formula I with a free radical initiator in the presence or absence of ethylenically unsaturated monomers. N-oxyl radical formers III, in which T is a polymeric chain are obtainable in a simple manner, for example by subjecting a small amount of monomers to free radical polymerization by means of a free radical polymerization initiator (e.g. peroxide, hydroperoxide and/or azo compound) in the presence of an N-oxyl radical I and then purifying the polymerization product by reprecipitation (cf. for example DE-A 19735225). T may comprise, for example, from 1 to 100.000, preferably from 3 to 50.000, monomer units. Those processes which are disclosed in U.S. Pat. No. 5,021,481 may be used analogously as further processes for preparation of novel N-oxyl radical formers.

The present invention furthermore relates to a process for the free radical polymerization of ethylenically unsaturated monomers, wherein the polymerization is carried out in the presence of N-oxyl radicals of formula I. Pure monomers or monomer mixtures can be polymerized by the novel process.

The novel process is carried out as a rule at elevated temperatures, for example from 50 to 100° C., preferably from 60 to 180° C. For carrying out the process, for example, a mixture (1) of either (i) nitroxyl radical and, if required, free radical initiator or (ii) nitroxyl radical former; and (2) at least one ethylenically unsaturated monomer can be heated. The reaction times are in general from 30 minutes to 6 days, in particular from 1 hour to 60 hours. The reaction can be terminated or frozen by cooling, for example, at room temperature. Thereafter, the polymer can be isolated and, if required, washed and dried.

Thermal initiation of the polymerization, dispensing with the addition of free radical initiator, is suitable, in particular in the polymerization of styrene or styrene-containing monomer mixtures.

The novel process is particularly suitable for the preparation of block copolymers. These are obtained by polymerizing successive different monomers or monomer mixtures of different compositions. In a preferred procedure of this process, at least a first monomer is polymerized in the presence of N-oxyl radicals to obtain an intermediate polymer, the intermediate polymer, is, if required, isolated and at least a second monomer is polymerized in the presence of the intermediate polymer.

Specifically, a preferred process is one in which
a) a mixture (1) of either (i) free radical initiator and nitroxyl radical or (ii) nitroxyl radical former; and (2) at least a first ethylenically unsaturated monomer is heated to obtain an intermediate polymer,
b) the intermediate polymer is, if required, isolated,
c) at least one second ethylenically unsaturated monomer differing from the first monomer is added to the intermediate polymer and the mixture is heated to obtain a block copolymer, and
d) the block copolymer is isolated and, if required, washed and dried.

To obtain the higher block copolymers step c) can be repeated once or several times, a third or further monomer being used instead of the second ethylenically unsaturated monomer. Instead of pure monomers, monomer mixtures may also be used. Different monomers are also understood as meaning monomer mixtures having different compositions. The blocks of a block copolymer obtained according to the invention can accordingly be homo- or copolymer blocks.

Isolation of the intermediate polymer is advisable when a very high purity, well defined block limits or high homogeneity within the blocks are desired. Isolating the intermediate polymer prevents unconverted first monomer from being incorporated into the forming block of the second monomer. Isolation of the intermediate polymer or of the block copolymer can be affected, for example by precipitation.

The monomers polymerizable according to the invention include olefins, e.g. ethylene, vinylaromatic monomers, such as styrene, α-methylstyrene, o-chlorostyrene or vinyltoluenes, 1,1- and 1,2-diphenylethylene, vinyl and vinylidene halides, such as vinyl and vinylidene chloride, esters of vinyl alcohol and monocarboxylic acids of 1 to 12-carbon atoms, such as vinyl acetate, vinyl propionate, vinyl-n-butyrate, vinyl laurate and commercially available monomers VEOVA® 9–11 (VEOVA X is a tradename of Shell and stands for vinyl esters of carboxylic acid, which are also referred to as Versatic® X acids), esters of allyl alcohol and monocarboxylic acids of 1 to 12 carbon atoms, such as allyl acetate, allyl propionate, allyl-n-butyrate and allyl laurate, esters of α,β-monoethylenically unsaturated mono- and dicarboxylic acids preferably of 3 to 6 carbon atoms, in particular acrylic acid, methacrylic acid, maleic acid, fumaric acid and itaconic acid, with alkanols of in general 1 to 12, preferably 1 to 8, in particular 1 to 4 carbon atoms, in particular methyl, ethyl, n-butyl, iso-butyl, tert-butyl and 2-ethylhexyl acrylate and methacrylate, dimethyl maleate or n-butyl maleate, nitriles of α,β-monoethylenically unsaturated carboxylic acid, such as acrylonitrile, and conjugated $C_{4-8}$-dienes, such as 1,3-butadiene and isoprene. However, α,β-monoethylenically unsaturated mono- and dicarboxylic acid of 3 to 6 carbon atoms and their amides, e.g. acrylic acid, methacrylic acid, maleic acid, fumaric acid, itaconic acid, acrylamide and methacrylamide, N-methylacrylamide, N-ethylacrylamide, N-isopropylacrylamide and N,N'-dimethylacrylamide, and furthermore vinylsulfonic acid and its water-soluble salts and N-vinylpyrrolidone are also suitable. This also applies to those monomers which usually increase the internal strength of the resulting polymer and which usually have an epoxy, hydroxyl or N-methylol group. Examples of these are N-alkylolamides of α,β-monoethylenically unsaturated carboxylic acids of 3 to 10 carbon atoms and their ethers with alkanols of 1 to 4 carbon atoms among which N-methylolacrylamide and N-methylolmethacrylamide are very particularly preferred.

In a preferred embodiment of the novel process, vinylaromatic monomers, dienes or (meth)acrylates or mixtures thereof are used as monomers. In particular, the monomers used are chosen from amongst styrene, α-methylstyrene, vinyltoluene, diphenylethylene, acrylonitrile, butadiene, isoprene, n-butyl acrylate, methyl methacrylate or mixtures thereof.

In a further preferred embodiment of the novel process, at least one vinylaromatic monomer, if required as a mixture with further monomers, is polymerized.

In a further preferred embodiment of the novel process, at least one diene, if required as a mixture with further monomers, is polymerized.

In a further preferred embodiment of the novel process, at least one (meth)acrylate, if required as a mixture with further monomers, is polymerized.

The novel process can be carried out as solution, mass, precipitation, suspension, emulsion, miniemulsion and microemulsion polymerization or inverse free radical emulsion polymerization. The polymerization can be carried out batchwise, semicontinuously or continuously.

Suitable free radical polymerization initiators are in principle those which are capable of initiating a free radical polymerization. These may be peroxides, hydroperoxides, peresters, percarbonates, persulfates, azo compounds or compounds having a labile carbon-carbon bond. There may be either oil-soluble or water-soluble and are adapted to the chosen polymerization medium or the chosen polymerization temperature in a manner known per se. Redox initiator systems are also suitable.

Specific examples of suitable initiators are hydrogen peroxide, tert-butyl hydropetoxide, di-tert-butyl peroxide, tert-amyl hydroperoxide, dibenzoyl peroxide, potassium, sodium or ammonium peroxodisulfate, methyl ethyl ketone peroxide, dilauryl peroxide, cumyl hydroperoxide, dicumyl peroxide and azobisisobutyronitrile. Redox initiator systems comprise, for example, sodium disulfite, sodium sulfite, ascorbic acid, isoascorbic acid, sodium formaldehyde sulfoxylate and the like in combination with suitable oxidizing agents, such as the abovementioned initiators.

The amount of free radical initiator is preferably from $10^{-6}$ to 33, in particular from $10^{-4}$ to 10, mol %, based on the monomers.

The amount of novel N-oxyl radicals or N-oxyl radical formers to be used for a controlled free radical polymerization is as a rule from $10^{-4}$ to 33, in general from 0.005 to 20, mol %, based on the molar amount of monomers which are subjected to free radical polymerization. The molar ratio of N-oxyl radicals to free radical centers which form in the decomposition of the polymerization initiator is as a rule chosen to be from 0.25 to 5, frequently from 0.4 to 4, for a controlled free radical polymerization.

Preferably, the polymers prepared by the novel process have a molecular weight of from about 500 to 500,000. The conversion of monomer to polymer may be up to 99% by weight.

In the emulsion polymerization and its variants (microemulsion, miniemulsion), the monomers are emulsified in water, for which purpose emulsifiers are present.

Suitable emulsifiers are the anionic, cationic and neutral (nonionic) emulsifiers known to a person skilled in the art. Anionic emulsifiers are, for example, alkali metal salts of higher fatty acids of 10 to 30 carbon atoms, such as palmitic, stearic and oleic acid, alkali metal salts of sulfonic acid of, for example, 10 to 16 carbon atoms, in particular sodium salts of alkanesulfonic or alkylarylsulfonic acids, alkali metal salts of monoesters of phthalic acid, and alkali metal salts of resin acids, such as abietic acids. Cationic emulsifiers are, for example, salts of long-chain, in particular unsaturated amines of 12 to 18 carbon atoms, or quaternary ammonium compounds having relatively long-chain olefin or paraffin radicals (i.e. salts of quaternized fatty amines). Neutral emulsifiers, are, for example, ethoxylated fatty alcohols, ethoxylated fatty acids or ethoxylated phenols and fatty esters of polyhydric alcohols, such as pentaerthritol or sorbitol. Initiators which were poorly soluble in the monomer but readily soluble in water are preferably used for the emulsion polymerization. Peroxosulfates, such as potassium, sodium or ammonium peroxodisulfate or redox systems are therefore preferably used.

Buffer substances, such as $Na_2HPO_4/NaH_2PO_4$ or sodium citrate/citric acid, may be used as further additives in the polymerization in order to establish an essentially constant pH. Furthermore, molecular weight regulators, for example mercaptans, such as tert-dodecyl mercaptan, or ethylhexyl thioglycolate, may be present. These further additives can be added continuously or batchwise at the beginning and/or during the preparation of the emulsion and/or during the polymerization.

In the miniemulsion polymerization, an emulsion is prepared from the monomers, water and the emulsifiers by allowing high shear forces to act. Homogenizers, which are known to persons skilled in the art, such as pressure homogenizers, apparatuses having a rotor-stator system or colloid mills or ultrasonic apparatuses are used for this purpose.

In the suspension polymerization and its variants (microsuspension), the monomers are dispersed in water, for which purpose protective colloids are present. Suitable protective colloids are cellulose derivatives, such as carboxymethylcellulose and hydroxymethylcellulose, poly-N-vinylpyrrolidone, polyvinyl alcohol and polyethylene oxide, anionic polymers, such as polyacrylic acid and the copolymers thereof and cationic polymers, such as poly-N-vinylimidazol. The amount of these protective colloids is preferably from 0.1 to 5% by weight, based on the total mass of the emulsion. Suitable protective colloids are described, for example, in Encyclopedia of Polymer Science and Engineering, Vol. 16, (1989) page 448, published by J. Wiley.

In the precipitation polymerization, the monomers used are soluble in the continuous phase (for example, solvent or solvent mixture) but insoluble or soluble only to a limited extent in the polymers formed and are therefore precipitated during the polymerization. Mass polymerizations in which the resulting polymer is insoluble in the monomer and is therefore precipitated are also possible.

In the mass polymerization, the monomers are polymerized without the addition of a reaction medium, with the use of said monomer-soluble initiates, i.e. the monomers are the reaction medium. Thermal initiation may also be effected.

In the solution polymerization, an organic solvent, such as toluene, cyclohexane, ethylbenzene or dimethyl sulfoxide, is used or is present for diluting the monomers.

The novel process can also be carried out as a combined process in which at least two of the polymerization processes described above are combined with one another. In particular, mass/solution, solution/precipitation, mass/suspension and mass/emulsion may be mentioned here, the first-mentioned being used at the beginning and the last-mentioned at the end.

Depending on the solubility behavior, the N-oxyl radical can be used either as such or in solution in organic solvents, such as alcohols, e.g. methanol and/or ethanol, ethyl acetate, dimethylformamide, toluene, ethylbenzene, cyclohexane or benzene or mixtures thereof. The addition of the N-oxyl radical in the form of a solution in a monomer or monomer mixture to be polymerized is also preferred.

By adding inorganic or organic acids, such as 3-indolylbutyric acid, indolylacetic acid or organic sulfonic acids, such as camphorsulfonic acid or p-toluenesulfonic acid (cf. U.S. Pat. No. 5,322,912) or by adding dimethyl sulfoxide (cf. U.S. Pat. No. 5,412,047) or 2-fluoro-1-methylpyridinium p-toluene sulfonate (cf. Macromolecules 28 (1995) 8453 et seq.) to the polymerization mixture, the polymerization rate of the novel process can as a rule be increased.

The novel process is usually carried out at an absolute pressure from atmospheric pressure to 60 bar, preferably up to 45 bar.

The polymers obtainable by the novel process can be used as such or mixed with other polymers and/or additives.

Such other polymers are in particular thermoplastic polymers. Such polymers include polyesters, such as polyethylene terephthalate and polybutylene terephthalate, polycarbonates, polyamides, polyoxymethylene, polystyrene, polyolefins, such as polyethylene and polypropylene, polyvinyl chloride and styrene copolymers, such as polystyrene acrylonitrile.

Suitable additives are conventional additives, for example lubricants or mold release agents, pigments, dyes, flame-proofing agents, antioxidants, light stabilizers, fibrous and pulverulent fillers or reinforcing agents or antistatic agents, and other additives, or mixtures thereof.

Suitable lubricants and mold release agents are, for example, fatty acids, such as stearic acids, stearyl alcohol, fatty esters of 6 to 20 carbon atoms, e.g. stearic esters, metal salts of fatty acids, e.g. calcium, aluminum and zinc stearate, fatty amides, such as stearamides, and silicone oils, montan waxes and those based on polyethylene and polypropylene, and furthermore hydrocarbon oils, paraffins and carboxylic esters obtained from long-chain carboxylic acids and ethanol, fatty alcohols, glycerol, ethane diol, pentaerythritol or other alcohols.

Pigments are, for example, titanium dioxide, phthalocyanines, ultramarine blue, iron oxides or carbon black, and the class comprising the organic pigments.

Dyes are understood as meaning all dyes which can be used for transparent, semitransparent or opaque coloring of polymers, in particular those which are suitable for coloring styrene copolymers. Such dyes are known to a person skilled in the art.

For example, the halogen-containing or phosphorus-containing compounds, magnesium hydroxide and other customary compounds, or mixtures thereof, known to persons skilled in the art, can be used as flameproofing agents.

Suitable antioxidants (heat stabilizers) are, for example, stearically hindered phenols, hydroquinones, various substituted members of this group, and mixtures thereof. They are commercially available, for example, as Topanol® or Irganox®.

Suitable light stabilizers are, for example, various substituted resorcinols, salicylates, benzotriazols, zinnamic acid compounds, organic phosphites and phosphonites, benzophenones, HALS (Hindered Amine Light Stabilizers), as commercially available, for example, as Tinuvin®.

Esters and/or amides of β-(3,5-di-tert-butyl-4-hydroxyphenyl) propionic acid and/or benzotriazol may likewise be used as stabilizers. Possible oxidants are mentioned in EP-A-698,637 and EP-A-669,367 by way of example. In particular, 2,6-di-tert-butyl-4-hydroxyphenyl) propionate and N,N'-di-(3,5-di-tert-butyl-4-hydroxyphenyl-propionyl) hexamethylenediamine may be used as phenolic antioxidants.

Examples of fibrous or pulverulent fillers are carbon fibers or glass fibers in the form of woven glass fabrics, glass mats or glass rovings, chopped glass, glass beads and wollastonite, particularly preferably glass fibers. When glass fibers are used, they may be provided with a size and an adhesion promoter for better compatibility with the blend components. The glass fibers can be incorporated both in the form of short glass fibers and in the form of rovings.

Suitable particulate fillers are carbon black, amorphous silica, magnesium carbonate (chalk), powdered quartz, mica, bentonite, talc, feldspar or in particular calcium silicates, such as wollastonite and kaolin.

Suitable antistatic agents are, for example, amine derivatives, such as N,N-bis(hydroxyalkyl)alkylamines or alkyleneamines, polyethylene glycol esters and glyceryl mono- and distearates, and mixtures thereof. The individual additives are used in the respective conventional amounts. Usually, the additives are used in an amount of from 0 to 50% by weight, based on the sum of block copolymers and additives.

Mixing of the polymers prepared according to the invention with the other polymers and/or additives is carried out continuously or batchwise by mixing methods known per.se, for example with melting in an extruder, Banbury mixer, kneader, rawmill or calendar. However, the components can also be mixed cold, and the mixture is not melted and homogenized until during the processing.

The mixtures obtained can, for example, be pelleted or granulated or can be processed by generally known methods, for example by extrusion, injection molding, expansion using blowing agents or calendaring.

The novel free radicals and free radical formers are furthermore suitable as inhibitors for suppressing undesired free radical polymerization of monomers, i.e. for stabilizing monomers (as stabilizers). The present invention therefore also relates to the use of the novel N-oxyl radicals for stabilizing ethylenically unsaturated monomers to undesired free radical polymerization. The concentrations used for this purpose are in general from 0.001 to 0.1 mol %, based on the monomers.

The novel free radicals and free radical formers are furthermore suitable for stabilizing inanimate organic material to light and heat. Organic material is to be understood as meaning, for example, cosmetic preparations, such as ointments and lotions, drug formulations, photographic recording materials, and in particular photographic emulsions, intermediates for plastics and coating materials, but in particular plastics and coating materials themselves. The novel free radicals or free radical formers can be used in particular for stabilizing plastics during their processing or use. They are added to the plastics, for example, during or before the processing.

The examples which follow illustrate the invention.

EXAMPLE 1

8,8-Dimethyl-10-oxa-7-aza-spiro[5.5]undecan-7-oxyl

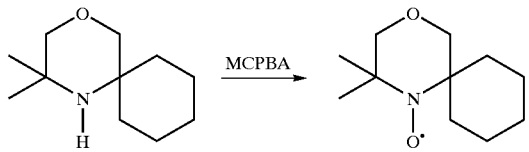

22.6 g 3-chloroperoxybenzoic acid are added in portions in the course of 2 hours at 0° C. to 11.7 g of 3,3-pentamethylene-5,5-dimethylmorpholine in 350 ml of methylene chloride. Stirring is then carried out for 12 hours, the temperature being increased to 23° C. 175 ml of saturated NaHCO$_3$-solution are then added. The organic phase is separated off and is extracted by shaking with 150 ml of 20% strength Na$_2$SO$_3$-solution and with three times 150 ml of water. The organic phase is dried with MgSO$_4$, filtered and evaporated down under reduced pressure. Yield: 12.3 g.

EXAMPLE 2

7,7-Dimethyl-9-oxa-6-aza-spiro[4.5]decan-6-oxyl

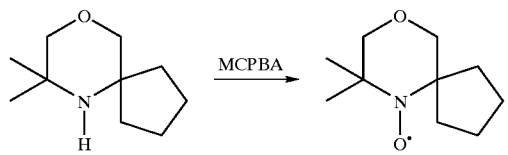

19.6 g of 3-chloroperoxybenzoic acid are added in portions in the course of 2 hours at 0° C. to 11.4 g of 3,3-tetramethylene-5,5-dimethylmorpholine in 200 ml of methylene chloride. Stirring is then carried for 12 hours, the temperature being increased to 23° C. Saturated NaHCO$_3$-solution is then added until the gas evolution stops. The organic phase is separated off and is extracted with 25 ml of 20% strength Na$_2$SO$_3$-solution and with three times 25 ml of water. The organic phase is dried with MgSO$_4$, filtered and evaporated down under reduced pressure. Yield: 12.1 g

EXAMPLE 3

Polymerization Examples

The following N-oxyl radicals were used:

1

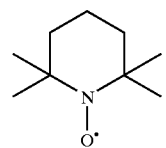

2

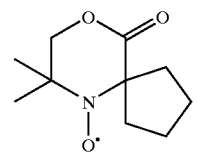

3

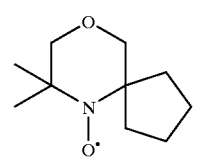

4

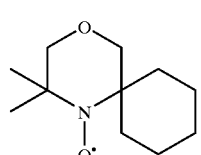

The experiments were carried out in the absence of solvent in sealed glass tubes. The total amount of each sample was 70 g. Each sample was degassed bypassing through nitrogen prior to sealing. The sealed sample tubes in aluminum safety containers were immersed in a thermostatted oil bath at the desired temperature. The experiments were carried out using styrene as monomer, benzoyl peroxide as initiator and in each case an N-oxyl radical. TEMPO (1) and the N-oxyl radical (2) were included for comparison. The table below shows the amounts used, the duration of polymerization, the conversion achieved, the number average molecular weight (<Mn>) and the polydispersity of the polymer.

| Styrene [g] | BPO [g] | 1* [g] | 2* [g] | 3 [g] | 4 [g] | T [°C.] | t [h] | Conversion [%][1] | <Mn> [g/mol] | PDI |
|---|---|---|---|---|---|---|---|---|---|---|
| 70 | 0.166 | 0.075 | — | — | — | 125 | 4 | solid | 50,500 | 1.44 |
| 70 | 0.166 | 0.098 | — | — | — | 125 | 4 | 49.8 | 43,400 | 1.35 |
| 70 | 0.166 | 0.113 | — | — | — | 125 | 4 | 22.5 | 15,400 | 1.26 |
| 70 | 0.166 | 0.128 | — | — | — | 125 | 4 | 14.2 | 20,600 | 1.24 |
| 70 | 0.166 | 0.150 | — | — | — | 125 | 4 | 7.6 | 7,100 | 1.27 |
| 70 | 0.166 | 0.188 | — | — | — | 125 | 4 | 2.8 | 2,800 | 1.69 |
| 70 | 0.166 | 0.112 | — | — | — | 110 | 5 | 5.9 | 7,400 | 1.50 |
| 70 | 0.166 | 0.112 | — | — | — | 110 | 8 | 17.4 | 17,900 | 1.38 |
| 70 | 0.166 | 0.112 | — | — | — | 110 | 16 | 45.7 | 41,000 | 1.28 |
| 70 | 0.166 | 0.112 | — | — | — | 110 | 40 | 89.0 | 64,800 | 1.33 |
| 70 | 0.166 | 0.112 | — | — | — | 125 | 1 | 1.6 | 3,906 | 2.02 |
| 70 | 0.166 | 0.112 | — | — | — | 125 | 2 | 12.2 | 11,910 | 1.34 |
| 70 | 0.166 | 0.112 | — | — | — | 125 | 5 | 47.2 | 36,790 | 1.34 |
| 70 | 0.166 | 0.112 | — | — | — | 125 | 8 | 66.2 | 46,500 | 1.35 |
| 70 | 0.166 | 0.112 | — | — | — | 125 | 16 | solid | 52,140 | 1.46 |
| 70 | 0.166 | — | 0.154 | — | — | 110 | 5 | 24.4 | 30,000 | 1.99 |
| 70 | 0.166 | — | 0.154 | — | — | 110 | 8 | 33.0 | 43,300 | 1.85 |
| 70 | 0.166 | — | 0.154 | — | — | 110 | 16 | 53.7 | 53,200 | 1.72 |
| 70 | 0.166 | — | 0.154 | — | — | 125 | 1 | 12.6 | 16,900 | 2.21 |
| 70 | 0.166 | — | 0.154 | — | — | 125 | 2 | 26.2 | 22,600 | 2.02 |
| 70 | 0.166 | — | 0.154 | — | — | 125 | 5 | 59.7 | 41,300 | 1.45 |
| 70 | 0.166 | — | 0.154 | — | — | 125 | 8 | solid | 48,600 | 1.43 |
| 70 | 0.166 | — | — | 0.090 | — | 126 | 4 | solid | 50,200 | 1.74 |
| 70 | 0.166 | — | — | 0.117 | — | 126 | 4 | 55.3 | 43,200 | 1.60 |
| 70 | 0.166 | — | — | 0.135 | — | 126 | 4 | 38.2 | 34,000 | 1.53 |
| 70 | 0.166 | — | — | 0.153 | — | 126 | 4 | 31.0 | 27,500 | 1.60 |
| 70 | 0.166 | — | — | 0.180 | — | 126 | 4 | 13.3 | 13,400 | 1.69 |
| 70 | 0.166 | — | — | 0.226 | — | 126 | 4 | 2.9 | 4,200 | 1.72 |
| 70 | 0.166 | — | — | 0.135 | — | 125 | 1 | 14.4 | 21,500 | 2.10 |
| 70 | 0.166 | — | — | 0.135 | — | 125 | 2 | 31.8 | 30,000 | 1.72 |
| 70 | 0.166 | — | — | 0.135 | — | 125 | 3 | solid | 45,300 | 1.54 |
| 70 | 0.166 | — | — | — | 0.143 | 110 | 2 | 18.7 | 23,800 | 2.01 |
| 70 | 0.166 | — | — | — | 0.143 | 110 | 5 | 32.7 | 33,300 | 1.67 |
| 70 | 0.166 | — | — | — | 0.143 | 110 | 8 | 42.2 | 40,200 | 1.58 |
| 70 | 0.166 | — | — | — | 0.143 | 110 | 16 | solid | 57,200 | 1.46 |
| 70 | 0.166 | — | — | — | 0.143 | 126 | 1 | 22.5 | 22,200 | 1.64 |
| 70 | 0.166 | — | — | — | 0.143 | 126 | 2 | 55.7 | 41,600 | 1.47 |
| 70 | 0.166 | — | — | — | 0.143 | 126 | 5 | solid | 50,600 | 1.46 |
| 70 | 0.166 | — | — | — | 0.143 | 126 | 8 | solid | 54,600 | 1.48 |

*Comparative Example
[1]"solid" means a conversion of >90%

We claim:

1. A process for the free radical polymerization of one or more ethylenically unsaturated monomers, said process comprising polymerizing one or more ethylenically unsaturated monomers in the presence of one or more N-oxyl radicals of formula II, wherein X is S, $NR^5$, O, SO or $SO_2$, $R^5$ is $C_1$–$C_{20}$-alkyl or $C_5$–$C_8$-cycloalkyl and $R^3$ and $R^4$ independently of one another, are $C_1$–$C_4$-alkyl, phenyl, naphthyl or an aromatic five-membered ring, or $R^3$ and $R^4$ together are —$(CH_2)_o$— and p and o, independently

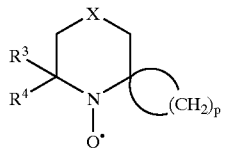

(II)

of one another, are an integer from 2 to 7.

2. The process as claimed in claim 1, wherein one or more different monomers are successively polymerized.

3. The process as claimed in claim 2, further comprising polymerizing at least one first monomer in the presence of the one or more N-oxyl radicals to obtain an intermediate polymer, isolating said intermediate polymer, and polymerizing at least one second monomer in the presence of said intermediate polymer.

4. The process as claimed in claim 1, further comprising initiating the polymerization by heating a mixture of one or more N-oxyl radical formers of formula III and at least one ethylenically unsaturated monomer,

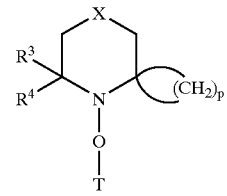

wherein

X, $R^3$, and $R^4$ are as defined in claim 1

T is a radical of the formula

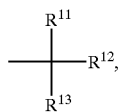

wherein $R^{11}$, $R^{12}$ and $R^{13}$, independently of one another, are hydrogen, $C_1$–$C_4$-alkyl, or phenyl, or a cyano or ester group, or a polymeric chain comprising units of ethylenically unsaturated monomers, wherein the N-oxyl radical former decomposes to a N-oxyl radical of the formula II and a free radical.

5. The process as claimed in claim 4, wherein one or more different monomers are successively polymerized.

6. The process as claimed in claim 5, further comprising
polymerizing at least one first monomer in the presence of the one or more N-oxyl radicals to obtain an intermediate polymer,
isolating said intermediate polymer, and
polymerizing at least one second monomer in the presence of said intermediate polymer.

7. The process as claimed in claim 4, wherein the process is conducted at a temperature ranging from 60 to 180° C.

8. The process as claimed in claim 4, wherein the process is conducted for a time ranging from 30 minutes to 6 days.

9. The process as claimed in claim 4 wherein the ethylenically unsaturated monomer is one or more monomer selected from the group consisting of a vinylaromatic monomer, a diene, and a (meth)acrylate.

10. The process as claimed in claim 4, wherein the ethylenically unsaturated monomer is one or more monomer selected from the group consisting of styrene, α-methylstyrene, vinyltoluene, diphenylethylene, acrylonitrile, butadiene, isoprene, n-butyl acrylate, and methyl methacrylate.

11. The process as claimed in claim 1, wherein the process is conducted at a temperature ranging from 60 to 180° C.

12. The process as claimed in claim 1, wherein the process is conducted for a time ranging from 30 minutes to 6 days.

13. The process as claimed in claim 1, wherein the ethylenically unsaturated monomer is one or more monomer selected from the group consisting of a vinylaromatic monomer, a diene, and a (meth)acrylate.

14. The process as claimed in claim 1, wherein the ethylenically unsaturated monomer is one or more monomer selected from the group consisting of styrene, α-methylstyrene, vinyltoluene, diphenylethylene, acrylonitrile, butadiene, isoprene, n-butyl acrylate, and methyl methacrylate.

* * * * *